United States Patent
Skinner

(10) Patent No.: US 6,315,737 B1
(45) Date of Patent: Nov. 13, 2001

(54) BIOPSY NEEDLE FOR A BIOPSY INSTRUMENT

(75) Inventor: Bruce A. J. Skinner, Sault Ste. Marie (CA)

(73) Assignee: Biopsy Needle Limited Partnership, Sault Ste. Marie (CA)

( * ) Notice: Subject to any disclaimer, the term of this patent is extended or adjusted under 35 U.S.C. 154(b) by 0 days.

(21) Appl. No.: 09/498,622

(22) Filed: Feb. 7, 2000

Related U.S. Application Data

(63) Continuation-in-part of application No. 09/002,472, filed on Jan. 2, 1998, now Pat. No. 6,022,324.

(51) Int. Cl.[7] .................................................. A61B 10/00
(52) U.S. Cl. ......................... 600/566; 600/567; 600/583; 606/167
(58) Field of Search .................................. 600/562, 564, 600/565, 566, 567, 568, 573, 583; 606/80, 167, 170, 171, 185

(56) References Cited

U.S. PATENT DOCUMENTS

| | | | |
|---|---|---|---|
| 3,850,158 | 11/1974 | Elias et al. | 128/2 B |
| 4,010,737 | 3/1977 | Vilaghy et al. | 128/2 B |
| 4,461,305 | 7/1984 | Cibley | 600/567 |
| 4,873,991 | 10/1989 | Skinner | 600/567 |
| 4,893,635 | 1/1990 | de Groot et al. | 600/567 |
| 4,903,709 | 2/1990 | Skinner | 600/567 |
| 4,909,249 | 3/1990 | Akkas et al. | 600/567 |
| 5,012,818 | 5/1991 | Joishy | 600/567 |
| 5,019,037 | 5/1991 | Wang et al. | 604/23 |
| 5,040,542 | 8/1991 | Gray | 600/567 |
| 5,060,658 | 10/1991 | Dejter, Jr. et al. | 600/567 |
| 5,146,921 | 9/1992 | Terwilliger et al. | 600/567 |
| 5,234,000 | 8/1993 | Hakky et al. | 600/567 |
| 5,257,632 | 11/1993 | Turkel et al. | 600/567 |
| 5,324,300 | 6/1994 | Elias et al. | 606/180 |
| 5,394,887 | 3/1995 | Haaga | 600/567 |
| 5,507,298 | 4/1996 | Schramm et al. | 600/567 |
| 5,511,556 | 4/1996 | DeSantis | 600/567 |
| 5,538,008 | * 7/1996 | Crowe | 600/564 |
| 5,560,373 | 10/1996 | De Santis | 600/566 |
| 5,769,086 | 6/1998 | Ritchart et al. | 600/566 |
| 5,807,277 | * 9/1998 | Swaim | 600/567 |
| 5,817,033 | 6/1998 | DeSantis et al. | 600/564 |
| 5,895,403 | * 4/1999 | Collinsworth | 606/184 |
| 5,922,000 | * 7/1999 | Chodorow | 606/167 |
| 5,928,162 | * 7/1999 | Giurtino et al. | 600/567 |

FOREIGN PATENT DOCUMENTS

| | | | |
|---|---|---|---|
| 2071212 | 6/1991 | (CA) . | |
| 2059875 | 8/1992 | (CA) . | |
| 1222669 | 6/1987 | (CA) | 128/2 |
| 1118655 | 2/1982 | (CA) | 128/82 |
| 44 38 333 C | 4/1996 | (DE) . | |
| 0 536 888 A | 4/1993 | (EP) . | |
| 96 09003 A | 3/1996 | (WO) . | |

OTHER PUBLICATIONS

Brochure entitled "BioAcess Marrow Biopsy System", Bio-Access Inc., 4000 Hudson Street, Baltimore, Maryland, 21224, U.S.A.

* cited by examiner

Primary Examiner—John P. Lacyk
Assistant Examiner—Charles Marmor, II
(74) Attorney, Agent, or Firm—Gowling Lafleur Henderson LLP

(57) ABSTRACT

A biopsy needle with a conduit for receiving a hard biopsy sample and a fluid biopsy sample. The conduit has a first cross-sectional area. The biopsy needle has an end with a penetrating bit operable for coring the hard biopsy sample. The end has a second cross-sectional area less than the first cross-sectional area. Therefore, the hard biopsy sample has a cross-sectional area substantially equal to the second cross-sectional area A space is thus left between the hard biopsy sample and the conduit when the hard biopsy sample is received therein. The biopsy needle has a retainer located at an interior of the conduit for holding the cored hard biopsy sample within the conduit. The biopsy needle also has an aperture on a sidewall of the conduit for aspirating the fluid biopsy sample into the space.

20 Claims, 3 Drawing Sheets

BIOPSY NEEDLE FOR A BIOPSY INSTRUMENT

This application is a continuation-in-part of U.S. patent application Ser. No. 09/002,472, filed Jan. 2, 1998, now U.S. Pat. No. 6,022,324.

FIELD OF THE INVENTION

The present invention relates to a biopsy needle. In particular, the present invention relates to a biopsy needle for retrieving a hard biopsy sample and a fluid biopsy sample, and a method of use and a biopsy instrument employing such a needle.

BACKGROUND OF THE INVENTION

Many biopsy needles and biopsy instruments are known. The biopsy needles of the prior art have been generally directed to bone biopsy needles and soft tissue biopsy needles. Biopsy needles are typically tubular stainless steel with a cutting end and aperture to receive a biopsy sample.

Bone biopsy needles are generally cumbersome and difficult instruments to use. As a result, biopsy procedures using bone biopsy needles are generally painful and traumatic. A bone biopsy generally involves taking both a bone and bone marrow samples. The doctor manually inserts a needle through the skin and into the bone. Because the bone is hard the needle is very difficult to insert and therefore requires a lot of strength on the part of the practitioner. The needle is inserted into the bone and then manipulated in an attempt to break off a piece of bone in the needle. A syringe is then placed on the end of the needle to aspirate the liquid bone marrow into the needle. Often the liquid bone marrow can not be properly aspirated into the needle because the hard bone biopsy sample is blocking the opening into the needle. Furthermore, the bone sample is difficult to retain in the needle. As a result, biopsies using such needles are often inadequate since the liquid bone marrow sample and the cored solid bone sample are not obtainable in a single operation, and the procedure must be repeated to get both biopsy samples.

A bone marrow biopsy needle is disclosed in U.S. Pat. No. 4,356,828 to Jamshidi. The needle disclosed by Jamshidi is a conduit with a tapered end for receiving a bone biopsy sample. The tapered end penetrates the bone and a core of the tissue passes into the opening of the needle. The needle is then manipulated to break off the cored bone. The fluid bone marrow sample is difficult to collect since the opening of the needle is effectively plugged by the cored bone sample.

A bone marrow surgical needle is disclosed in U.S. Pat. No. 5,012,818 to Joishy. Joishy discloses a biopsy needle with a tubular outer sleeve in which two separate conduits are contained. The first conduit is used to obtain the solid bone biopsy sample. The second conduit is used to obtain the fluid bone marrow biopsy sample. Each conduit contains two removable stylets. The handle of the Joishy needle can be opened to remove the stylets from each conduit and attach a syringe to aspirate the bone marrow biopsy sample. The needle is tapered at the cutting end to assist in breaking off and retaining the bone biopsy sample. During use, the needle is pushed into the bone and the handle of the biopsy needle is opened. The first stylet is then removed thereby leaving an opening in the first conduit to receive a solid bone biopsy sample and the handle is again closed. The needle is then pushed further into the bone and the hard bone biopsy sample enters the first conduit. The handle is again opened and the second stylet is removed from the second conduit. A syringe is attached to second conduit at the handle and the bone marrow biopsy sample is aspirated through the second conduit and into the syringe. The needle is then manipulated to assist in breaking off the bone biopsy sample and then removed from the subject.

The Joishy needle requires a sleeve with two conduits and two removable stylets within the conduits. The biopsy procedure requires multiple steps to perform and therefore can be time-consuming. Also, the manufacture of such a complex needle can be difficult and costly.

Many soft-tissue biopsy needles are known. Many soft tissue biopsy needles of the prior art are generally known as tru-cut type needles. Tru-cut needles have a gutter drilled out of one end of the needle and a cannula or sleeve which slides over the gutter. After the tru-cut needle is inserted into the soft tissue, the soft tissue falls into the gutter. The sleeve is then pushed forward over the gutter slicing the tissue off into the gutter. As the true-cut needle is withdrawn, the tissue is maintained in the gutter.

Soft tissue needles of the prior art are not suitable for bone biopsies. Generally, the soft tissue needles are not strong enough to withstand the force on the needle necessary to penetrate the bone. Furthermore, the bone tissue does not fall into the gutter of the needle and therefore a bone biopsy sample can not be collected using such a needle. Soft-tissue biopsy needles are further unsuitable for bone biopsies since there is no means for obtaining the required liquid bone marrow sample in the needle.

U.S. Pat. No. 5,324,300 to Elias discloses a biopsy instrument for removing hard tissue samples. Elias discloses a biopsy needle with an outer sleeve and an inner guide pin within the sleeve. Elias also discloses a biopsy needle that has an outer sleeve with a serrated edge, a conduit located within the sleeve, and an inner guide pin within the conduit. The needle can be rotatably inserted into the patient using a motorized drill. This instrument requires multiple steps to retrieve a bone marrow biopsy sample and therefore can be time-consuming. Also, the manufacture of such a complex needle can be difficult and costly.

It is desirable to provide a biopsy needle to effectively sample both a hard biopsy sample and a fluid biopsy sample in a single conduit. Furthermore, it is desirable to provide a biopsy needle that can be used to obtain a bone sample and a liquid bone marrow sample in a single biopsy procedure. It is also desirable to provide a biopsy instrument that makes the biopsy process less traumatic and painful. Further, it is desirable to provide a biopsy instrument that requires less time to retrieve a biopsy sample and is more reliable, reducing the risk of requiring multiple procedures.

SUMMARY OF THE INVENTION

It is an object of the present invention to provide a biopsy needle that obviates or mitigates at least one of the disadvantages of the prior art, and a biopsy instrument employing such a needle.

In one aspect of the invention there is provided a biopsy needle with a conduit for receiving a hard biopsy sample and a fluid biopsy sample. The conduit has a first cross-sectional area. The biopsy needle has an end with a penetrating bit operable for coring the hard biopsy sample. The end has a second cross-sectional area less than the first cross-sectional area. Therefore, the hard biopsy sample has a cross-sectional area substantially equal to the second cross-sectional area. A space is thus left between the hard biopsy sample and the conduit when the hard biopsy sample is received therein.

The biopsy needle has a retainer located at an interior of the conduit for holding the cored hard biopsy sample within the conduit. The biopsy needle also has an aperture on a sidewall of the conduit for aspirating the fluid biopsy sample into the space.

In a second aspect of the invention there is provided a biopsy instrument for obtaining a hard biopsy sample and a fluid biopsy sample. The biopsy instrument has a biopsy needle with a conduit for receiving a hard biopsy sample and a fluid biopsy sample. The conduit has a first cross-sectional area. The biopsy needle has an end with a penetrating bit operable for coring the hard biopsy sample. The end has a second cross-sectional area less than the first cross-sectional area. Therefore, the hard biopsy sample has a cross-sectional area substantially equal to the second cross-sectional area. A space is thus left between the hard biopsy sample and the conduit when the hard biopsy sample is received therein. The biopsy needle has a retainer located at an interior of the conduit for holding the cored hard biopsy sample within the conduit. The biopsy needle also has an aperture on a sidewall of the conduit for aspirating the fluid biopsy sample into the space. The biopsy instrument has a drill for rotating the biopsy needle to permit penetration of the hard biopsy sample. The biopsy instrument also has an aspirator for drawing the fluid biopsy sample into the space.

In another aspect of the invention there is provided a method for obtaining a hard biopsy sample and a fluid biopsy sample. A biopsy needle having a conduit for receiving a hard biopsy sample and a fluid biopsy sample is provided. The hard biopsy sample is cored to leave a space between the hard biopsy sample and an interior sidewall of the conduit. The hard biopsy sample is retained within the conduit. The fluid biopsy sample is aspirated into the space.

In another aspect of the invention there is provided a biopsy kit for obtaining a hard biopsy sample and a fluid biopsy sample. The biopsy kit has a biopsy needle with a conduit for receiving a hard biopsy sample and a fluid biopsy sample. The conduit has a first cross-sectional area. The biopsy needle has an end with a penetrating bit operable for coring the hard biopsy sample. The end has a second cross-sectional area less than the first cross-sectional area. Therefore, the hard biopsy sample has a cross-sectional area substantially equal to the second cross-sectional area. A space is thus left between the hard biopsy sample and the conduit when the hard biopsy sample is received therein. The biopsy needle has a retainer located at an interior of the conduit for holding the cored hard biopsy sample within the conduit. The biopsy needle also has an aperture on a sidewall of the conduit for aspirating the fluid biopsy sample into the space. The kit also has an aspirator for drawing the fluid biopsy sample into the space.

BRIEF DESCRIPTION OF THE DRAWINGS

Preferred embodiments of the present invention will now be described, by way of example only, with reference to the attached Figures wherein.

DETAILED DESCRIPTION OF THE INVENTION

Figure 1:
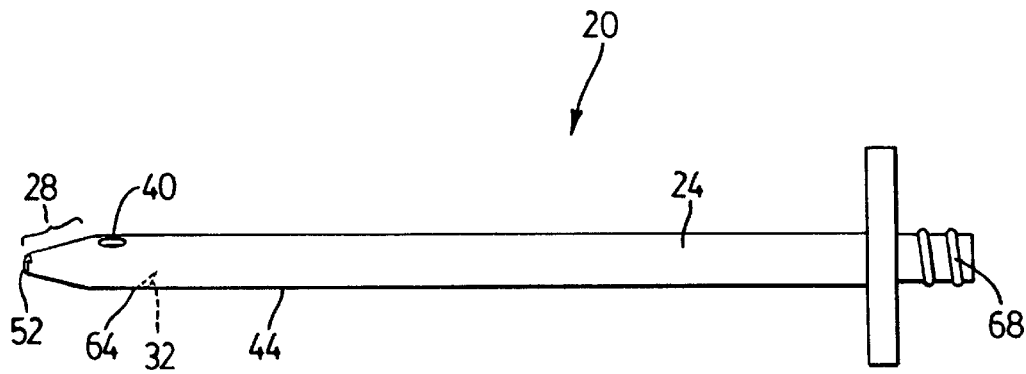
FIG. 1 is a side view of the biopsy needle, in accordance with an embodiment of the present invention.
Figure 2:
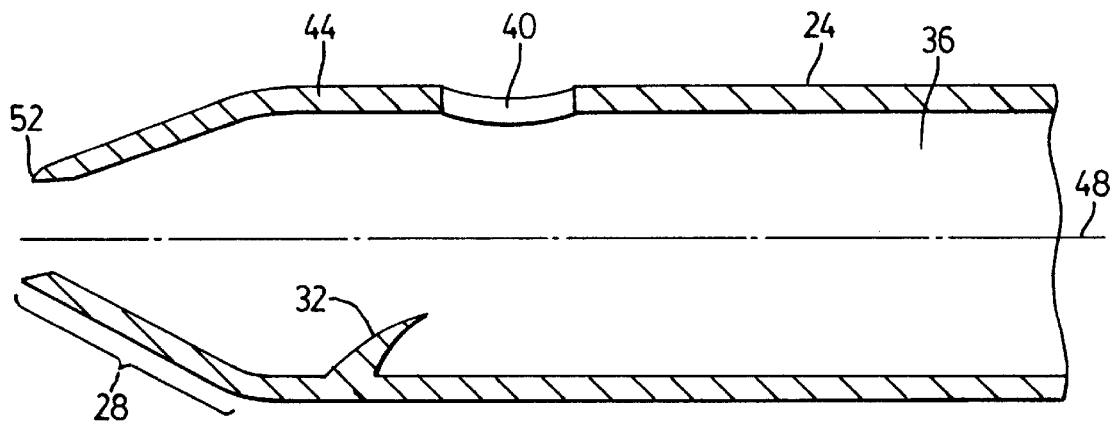
FIG. 2 is an axial cross-section of a portion of the biopsy needle of FIG. 1.

Referring to FIGS. 1 and 2, a biopsy needle according to an embodiment of the present invention is indicated generally at 20. FIG. 1 is a side view of biopsy needle 20. FIG. 2 shows an axial cross-section of a portion of needle 20 having an axis 48. Biopsy needle 20 can be used to perform tissue biopsies, particularly to retrieve a hard biopsy sample such as bone tissue, and a fluid biopsy sample such as bone marrow in a single operation. A hard biopsy sample, referred to herein, is not limited to a bone biopsy sample and can include any non-fluid tissue biopsy sample. Needle 20 generally consists of a conduit 24, an end 28 integrally formed with conduit 24, a retainer 32 located at an interior "passage" 36 of conduit 24, and an aperture 40 through conduit 24.

Conduit 24 is a tube formed by a sidewall 44 defining the interior or passage 36. Sidewall 44 has a wall thickness sufficient to withstand rotational, compressive and bending forces that can arise during the use of biopsy needle 20, particularly during a drilling operation as will be explained below. In the present embodiment, needle 20 is a medical grade stainless steel but other appropriate materials can be used as will be apparent to those of skill in the art.

End 28 is a section of needle 20 wherein the cross-sectional area is reduced from the first cross-sectional area of conduit 24 to a penetrating bit 52 having a second cross-sectional area. Typically biopsy needle 20 is approximately 10 cm in length. End 28 is generally ⅒ the length of biopsy needle 20. The diameter is generally reduced from 0.5 cm at conduit 24 to 0.45 cm or less at penetrating bit 52. It will be understood by those skilled in the art, however, that the size and proportions of biopsy needle 20 may vary depending on the size of the sample required, the target organ or bone and the subject. Penetrating bit 52 can be any edge suitable for cutting a hard biopsy material. According to one embodiment of the present invention, end 28 is integral with conduit 24 and is tapered toward a penetrating bit 52. Bit 52 is a substantially circular, serrated cutting edge that defines an opening 56. Alternatively, bit 52 can also be a sharp edge suitable for cutting through a hard biopsy material, as will occur to those of skill in the art. In another alternative, bit 52 can have a single tooth for cutting the hard biopsy material.

Figure 3:
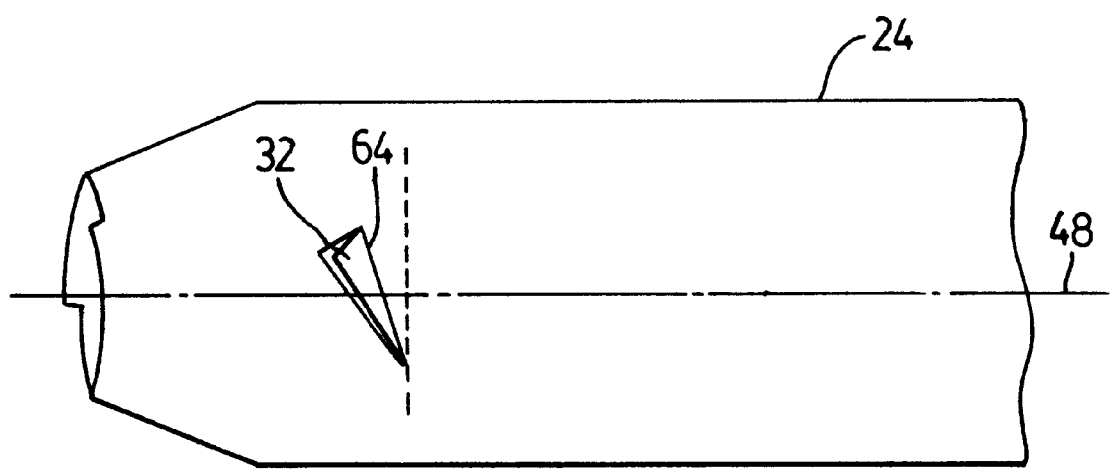
FIG. 3 is a side view of a portion of the biopsy needle of FIG. 1.

Retainer 32 can be any projection into interior 36 of conduit 24, suitable to retain a hard biopsy sample within conduit 24 and to prevent rearward movement of the sample when needle 20 is withdrawn from a subject. In one aspect of the present invention, retainer 32 can be a substantially triangular flap projecting into interior 36. However, retainer 32 can also be formed directly on the interior surface of conduit 24. For example, retainer 32 can be formed by depressing a flap, cut into sidewall 44, toward interior 36 along a fold line 64. Referring to FIG. 3, generally, fold line 64 is at an oblique angle with respect to axis 48 such that retainer 32 causes a spiral thread to be grooved into the surface of a hard biopsy sample and pull hard biopsy sample into interior 36 when needle 20 is rotatably inserted or drilled into a subject. Preferably, fold line 64 is at an angle of between 5 and 45 degrees with respect to the normal to axis 48. More preferably, fold line 64 is at an angle of approximately 20 degrees with respect to the normal to axis 48. Referring now to FIG. 2, in the current embodiment, retainer 32 projects a distance of less than approximately 30% of the diameter into interior 36 for a bone biopsy sample. As would occur to those of skill in the art, retainer 32 can project further into interior 36 depending on the tissue being sampled.

Aperture 40 can be any shape and size of hole suitable for a fluid biopsy sample to pass through when aspirated. Also, aperture 40 can be located at any position suitable for insertion within a target organ for aspiration of a fluid biopsy sample such that the source of the chosen fluid sample is adjacent to aperture 40. In the present illustration, aperture 40 is substantially circular and is generally smaller than the cross-sectional area of interior 36. Alternatively, aperture 40 can be defined by the hole left in sidewall 44 when retainer 32 is depressed inwardly. Specifically, when retainer 32 is formed by depressing a flap cut into sidewall 44, aperture 40 is created where the flap is cut away in sidewall 44. Equally, a plurality of apertures 40 can be provided in conduit 24 for more efficient collection of the fluid biopsy sample.

Opposite end 28 of conduit 24 is a connector 68. Connector 68 can be any portion suitable for attachment to an aspirator 72, such as a standard syringe. In the current illustration, connector 68 is threaded for attachment of aspirator 72.

Figure 4:
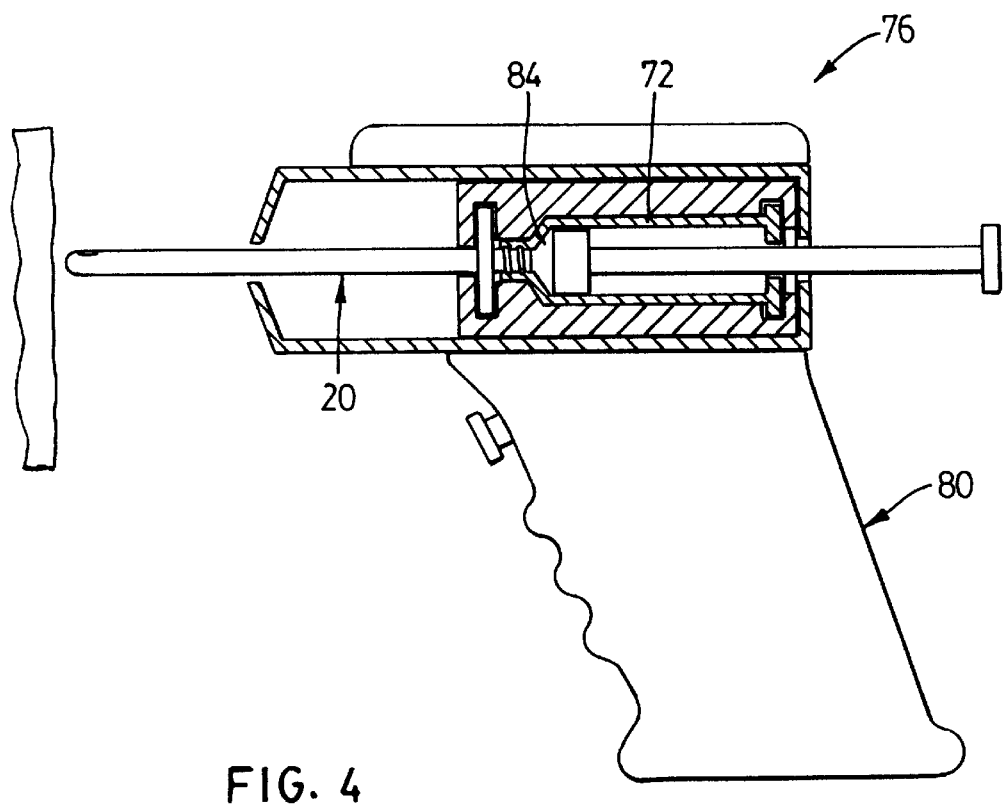
FIG. 4 is a sectional view of the biopsy instrument, in accordance with an embodiment of the present invention.

Referring to FIG. 4, a biopsy instrument according to a further aspect of the present invention is indicated generally at 76. Biopsy instrument 76 is preferably used to retrieve a hard biopsy sample such as a bone and a fluid biopsy sample such as bone marrow. Biopsy instrument 76 comprises a biopsy needle 20 as shown in FIG. 1, a drill 80 for rotating the biopsy needle, and an aspirator 72 for drawing the fluid biopsy sample into conduit 24.

Drill 80 can be any mechanism suitable for rotating biopsy needle 20 to penetrate the hard biopsy sample. According to one embodiment of the present invention, drill 80 is a motorized, hand-held instrument, suitable for medical use. Alternatively, drill 80 can be manually driven.

Aspirator 72 can be any apparatus suitable for drawing the fluid biopsy sample into interior 36. In the illustrated embodiment of the invention in FIG. 4, aspirator 72 is a syringe with a chamber 84 for collecting the fluid biopsy sample. Alternatively, aspirator 72 can be a pump with a chamber connected to biopsy needle 20.

The operation of biopsy needle 20 in retrieving a bone biopsy sample and a bone marrow biopsy sample will now be described with reference to the foregoing and the attached Figures.

Figure 5:
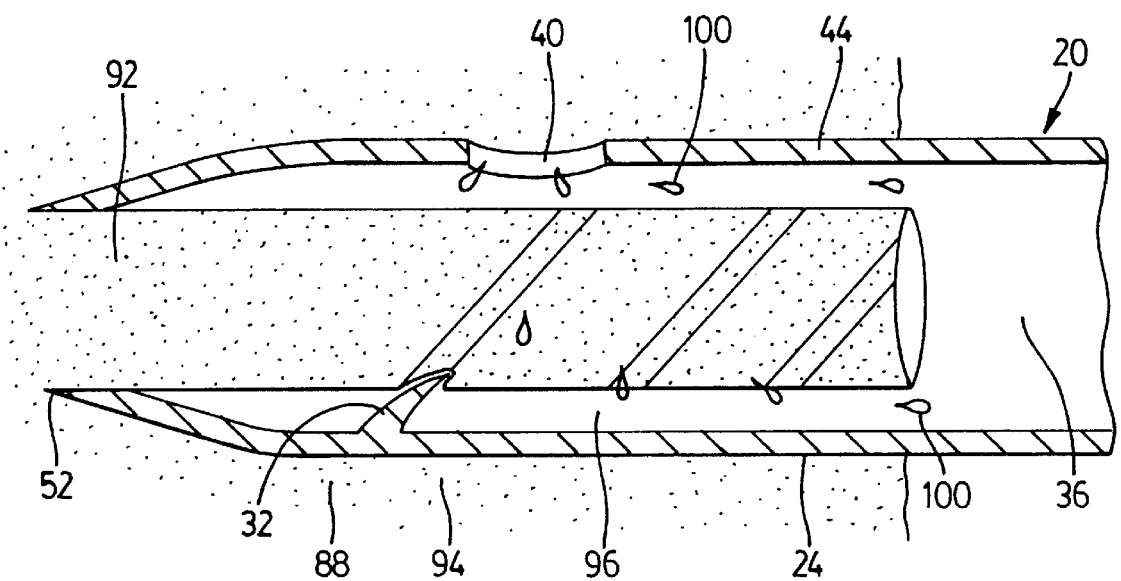
FIG. 5 is an axial cross-section of a portion of the biopsy needle of FIG. 1 when inserted into a target bone.

Referring to FIG. 5, an axial cross-section of a portion of needle 20 during use, biopsy needle 20 is inserted into a subject and bit 52 rotatably cuts into a target bone 88. The serrations on bit 52 assist in cutting through bone 88 when rotatably drilling therethrough. As bit 52 cuts into bone 88, a cored bone biopsy sample 92 enters interior 36 through opening 56. As drilling of needle 20 continues into target bone 88, cored bone biopsy sample 92 extends past retainer 32 and retainer 32 causes a spiral thread to be grooved into the surface of cored bone biopsy sample 92 to pull the cored sample into interior 36. When sufficient penetration of needle 20 is attained, cored bone biopsy sample 92 extends past aperture 40 and aperture 40 is within a bone marrow cavity 94 of target bone 88.

The cross-sectional area of cored bone biopsy sample 92 is substantially equal to the area of opening 56. The cross-sectional area of cored bone biopsy sample 92 is thus less than the cross sectional area of interior 36 in conduit 24. Therefore, a space 96 is left between cored bone biopsy sample 92 and sidewall 44. A bone marrow biopsy sample 100 is drawn from the bone and through aperture 40. The bone marrow is drawn through space 96 and into chamber 84 of aspirator 72. In a preferred embodiment, aspirator 72 is a syringe. Alternatively, the bone marrow can be aspirated using a vacuum pump and chamber, or other suitable means.

When bone marrow biopsy sample 100 is collected, needle 20 is withdrawn from target bone 88 and removed from the subject. Cored bone biopsy sample 92 breaks off and remains in interior 36 since retainer 32 prevents bone biopsy sample 92 from being pulled from interior 36. Thus retainer 32 also assists in severing bone biopsy sample 92 from target bone 88 when needle 20 is withdrawn from the subject. The cored bone sample and bone marrow retained in chamber 84 can then be analyzed by conventional methods.

It will now be understood by those skilled in the art that needle 20 and aspirator 72 can be packaged in a single sterilized kit for obtaining a hard biopsy sample and a fluid biopsy sample.

The present invention provides a novel biopsy needle for retrieving a hard biopsy sample such as bone tissue and a fluid biopsy sample such as bone marrow. In one embodiment, there is provided a biopsy needle with a conduit, and end integrally formed with the conduit, a retainer to prevent the biopsy sample from being pulled from the interior when removing the biopsy needle from the target organ or tissue, and an aperture for aspirating the fluid biopsy sample into and through the conduit. The needle can be rotatably inserted into the subject, the hard biopsy sample can be collected and the fluid biopsy sample can be aspirated in the interior of a single conduit. The retainer assists in breaking the hard biopsy sample away from the target organ and retaining the hard biopsy sample in the conduit. This can reduce the risk of losing the biopsy sample when removing the biopsy needle from the subject and therefore requiring an additional attempt to retrieve a sample. The present invention can make it easier for an operator to reliably obtain a tissue sample and thereby decrease the required skill of the operator. The use of a single conduit for retrieving both a hard biopsy sample and a fluid biopsy sample can reduce the number of steps in the manual process and can reduce the time required for a biopsy procedure. Also, the use of the present invention can reduce pain associated with such a biopsy procedure and increase patient comfort. Further, use of a single conduit to retrieve both a hard biopsy sample and a fluid biopsy sample can reduce the cost of the biopsy needle.

While the embodiments discussed herein are directed to particular implementations of the present invention, it will be apparent that the subsets and variations to these embodiments are within the scope of the invention. For example, the size or dimensions of the biopsy needle can differ from above. Alternatively, the shape, location and orientation of the aperture can differ. Similarly, the shape, location and orientation of the retainer can differ. More than one aperture or retainer can be present. The shape of the end can differ, being rounded, curved or odd shaped. Similarly, the shape of the penetrating bit can differ. The shape of any of the features can differ while still performing the same function.

I claim:

1. A biopsy needle, comprising:
   a conduit for receiving a hard biopsy sample and a fluid biopsy sample, the conduit having a single passage therethrough of a first cross-sectional area;
   an end with a penetrating bit operable for coring the hard biopsy sample, the end defining an opening having a second cross-sectional area less than the first cross-sectional area, such that the hard biopsy sample has a cross-sectional area substantially equal to the second cross-sectional area, thereby leaving a space between the hard biopsy sample and the conduit when the hard biopsy sample is received therein;

a retainer extending into said passage for holding the cored hard biopsy sample within the conduit; and an aperture extending through a sidewall of the conduit and fluidly communicating with said space for aspirating the fluid biopsy sample into the space.

2. The biopsy needle according to claim 1, wherein the hard biopsy sample is bone tissue.

3. The biopsy needle according to claim 2, wherein the fluid biopsy sample is bone marrow.

4. The biopsy needle according to claim 1, wherein the end is tapered from the conduit to the bit.

5. The biopsy needle according to claim 1, wherein the retainer is formed by depressing a flap cut into the sidewall, toward the interior.

6. The biopsy needle according to claim 5, wherein the flap is triangular.

7. The biopsy needle according claim 5, wherein the aperture is defined by the cut in the sidewall of the conduit.

8. The biopsy needle according to claim 1, wherein the bit is serrated.

9. The biopsy needle according to claim 1, wherein there are a plurality of apertures.

10. A biopsy instrument for obtaining a hard biopsy sample and a fluid biopsy sample, the biopsy instrument comprising:

a biopsy needle having a conduit for receiving a hard biopsy sample and a fluid biopsy sample, the conduit having a first cross-sectional area, an end with a penetrating bit operable for coring the hard biopsy sample, the end having a second cross-sectional area less than the first cross-sectional area, such that the hard biopsy sample has a cross-sectional area substantially equal to the second cross-sectional area, thereby leaving a space between the hard biopsy sample and the conduit when the hard biopsy sample is received therein; a retainer located at an interior of the conduit, the retainer for holding the cored hard biopsy sample within the conduit; and an aperture on a sidewall of the conduit for aspirating the fluid biopsy sample into the space;

a drill for rotating the biopsy needle to permit penetration of the hard biopsy sample; and an aspirator for drawing the fluid biopsy sample into the space.

11. The biopsy instrument according to claim 10, wherein the hard biopsy sample is bone tissue.

12. The biopsy instrument according to claim 11, wherein the fluid biopsy sample is bone marrow.

13. The biopsy instrument according to claim 10, wherein the end of the needle is tapered from the conduit to the bit.

14. The biopsy instrument according to claim 10, wherein the retainer is formed by depressing a flap cut into the sidewall, toward the interior.

15. The biopsy instrument according to claim 14, wherein the flap is triangular.

16. The biopsy instrument according claim 14, wherein the aperture is defined by the cut in the sidewall of the conduit.

17. The biopsy instrument according to claim 10, wherein the bit is serrated.

18. The biopsy instrument according to claim 10, wherein there are a plurality of apertures.

19. A method for obtaining a hard biopsy sample and a fluid biopsy sample comprising the steps of:

providing a biopsy needle having a conduit for receiving both a hard biopsy sample and a fluid biopsy sample, coring the hard biopsy sample, to leave a space between the hard biopsy sample and an interior sidewall of the conduit;

retaining the hard biopsy sample within the conduit aspirating a fluid biopsy sample into the space.

20. A sterile kit for obtaining a hard biopsy sample and a fluid biopsy sample, the kit comprising:

a biopsy needle having a conduit for receiving a hard biopsy sample and a fluid biopsy sample, the conduit having a single passage therethrough of a first cross-sectional area, an end with a penetrating bit operable for coring the hard biopsy sample, the end defining an opening having a second cross-sectional area less than the first cross-sectional area, such that the hard biopsy sample has a cross-sectional area substantially equal to the second cross-sectional area, thereby leaving a space between the hard biopsy sample and the conduit when the hard biopsy sample is received therein; a retainer extending into said passage for holding the cored hard biopsy sample within the conduit; and an aperature extending through a sidewall of the conduit and fluidly communicating with said space for aspiring the fluid biopsy sample into the space; and an aspirator for drawing the fluid biopsy sample into the space.

* * * * *